United States Patent
Perez-Cruet et al.

(10) Patent No.: US 7,666,211 B2
(45) Date of Patent: Feb. 23, 2010

(54) VERTEBRAL DISC ANNULAR FIBROSIS TENSIONING AND LENGTHENING DEVICE

(75) Inventors: Miquelangelo J. Perez-Cruet, Bloomfield, MI (US); John R. Pepper, Cheshire, CT (US); John A. Miller, Bloomfield Village, MI (US)

(73) Assignee: MI4SPINE, LLC, Bloomfield Hills, MI (US)

( * ) Notice: Subject to any disclaimer, the term of this patent is extended or adjusted under 35 U.S.C. 154(b) by 463 days.

(21) Appl. No.: 11/646,750

(22) Filed: Dec. 28, 2006

(65) Prior Publication Data
US 2008/0161931 A1 Jul. 3, 2008

(51) Int. Cl.
*A61B 17/70* (2006.01)
(52) U.S. Cl. .................. 606/250; 606/251; 606/253; 606/246
(58) Field of Classification Search ............... 606/246, 606/300–321, 90, 250–276; 411/14.5; 623/17.11–17.16
See application file for complete search history.

(56) References Cited

U.S. PATENT DOCUMENTS

| | | | |
|---|---|---|---|
| 4,759,769 A | 7/1988 | Hedman et al. |
| 4,931,055 A | 6/1990 | Bumpus et al. |
| 5,047,029 A | 9/1991 | Aebi et al. |
| 5,360,430 A | 11/1994 | Lin |
| 5,360,431 A | 11/1994 | Puno et al. |
| 5,423,816 A | 6/1995 | Lin |
| 5,443,467 A | 8/1995 | Biedermann et al. |
| 5,545,166 A | 8/1996 | Howland |
| 5,613,968 A | 3/1997 | Lin |
| 5,628,740 A | 5/1997 | Mullane |
| 5,672,175 A | 9/1997 | Martin |
| 5,688,275 A | 11/1997 | Koros et al. |
| 5,702,393 A | 12/1997 | Pfaifer |
| 5,733,284 A | 3/1998 | Martin |
| 5,782,831 A | 7/1998 | Sherman et al. |
| 6,162,223 A | 12/2000 | Orsak et al. |
| 6,241,730 B1 | 6/2001 | Alby |
| 6,267,764 B1 | 7/2001 | Elberg |
| 6,641,583 B2 | 11/2003 | Shluzas et al. |

(Continued)

FOREIGN PATENT DOCUMENTS

EP 0 282 161 A1 9/1988

(Continued)

OTHER PUBLICATIONS www.zimmer.com, Zimmer Spine, "Dynesys® Dynamic Stabilization System", 4 pgs.

*Primary Examiner*—Eduardo C Robert
*Assistant Examiner*—Christina Negrelli
(74) *Attorney, Agent, or Firm*—John A. Miller; Miller IP Group, PLC

(57) ABSTRACT

A vertebral disc annular fibrosis tensioning and lengthening device that restores the loss of disc height as a result of disc degeneration and other factors. The vertebral disc annular fibrosis tensioning and lengthening device includes pedicle screws having heads with cup-shaped cavities. The pedicle screws are threaded into the vertebral bodies of adjacent vertebrae through the pedicles so that open parts of the heads of the pedicle screws face each other. A spring is inserted into the cup-shaped cavities in compression so that the spring bias forces the pedicle screws apart, thus increasing the height of the disc space.

26 Claims, 4 Drawing Sheets

U.S. PATENT DOCUMENTS

| | | |
|---|---|---|
| 6,887,242 B2 | 5/2005 | Doubler et al. |
| 6,966,910 B2 | 11/2005 | Ritland |
| 6,989,011 B2 | 1/2006 | Paul et al. |
| 7,029,475 B2 | 4/2006 | Panjabi |
| 7,083,621 B2 | 8/2006 | Shaolian et al. |
| 7,291,150 B2 | 11/2007 | Graf |
| 7,361,196 B2 | 4/2008 | Fallin et al. |
| 2003/0009226 A1 | 1/2003 | Graf |
| 2003/0109880 A1 | 6/2003 | Shirado et al. |
| 2003/0220643 A1 | 11/2003 | Ferree |
| 2004/0002761 A1 | 1/2004 | Rogers et al. |
| 2004/0024461 A1 | 2/2004 | Ferree |
| 2004/0049189 A1 | 3/2004 | Le Couedic et al. |
| 2004/0049190 A1 | 3/2004 | Biedermann et al. |
| 2004/0049279 A1 | 3/2004 | Sevrain |
| 2004/0073215 A1 | 4/2004 | Carli |
| 2004/0116927 A1 | 6/2004 | Graf |
| 2004/0225289 A1 | 11/2004 | Biedermann et al. |
| 2005/0004674 A1 | 1/2005 | Senegas et al. |
| 2005/0038433 A1 | 2/2005 | Young |
| 2005/0056979 A1 | 3/2005 | Studer et al. |
| 2005/0065514 A1 | 3/2005 | Studer |
| 2005/0085815 A1 | 4/2005 | Harms et al. |
| 2005/0165396 A1 | 7/2005 | Fortin et al. |
| 2005/0203519 A1 | 9/2005 | Harms et al. |
| 2006/0015100 A1 | 1/2006 | Panjabi et al. |
| 2006/0036240 A1 | 2/2006 | Colleran et al. |
| 2006/0052786 A1 | 3/2006 | Dant et al. |
| 2006/0079896 A1 | 4/2006 | Kwak et al. |
| 2006/0084991 A1 | 4/2006 | Borgstrom et al. |
| 2006/0129147 A1 | 6/2006 | Biedermann et al. |
| 2006/0189983 A1 | 8/2006 | Fallin et al. |
| 2006/0189984 A1 | 8/2006 | Fallin et al. |
| 2006/0212033 A1 | 9/2006 | Rothman et al. |
| 2006/0229608 A1 | 10/2006 | Foster et al. |
| 2006/0282077 A1 | 12/2006 | Labrom et al. |
| 2006/0282080 A1 | 12/2006 | Albert et al. |
| 2007/0032123 A1 | 2/2007 | Timm et al. |
| 2007/0043356 A1 | 2/2007 | Timm et al. |
| 2007/0049936 A1 | 3/2007 | Colleran et al. |
| 2007/0073289 A1 | 3/2007 | Kwak et al. |
| 2007/0088359 A1 | 4/2007 | Woods et al. |
| 2007/0093814 A1 | 4/2007 | Callahan, II et al. |
| 2007/0100341 A1 | 5/2007 | Reglos et al. |
| 2007/0112427 A1 | 5/2007 | Christy et al. |
| 2007/0123865 A1 | 5/2007 | Schlapfer et al. |
| 2007/0203446 A1 | 8/2007 | Biedermann et al. |
| 2007/0233095 A1 | 10/2007 | Schlaepfer |
| 2007/0233123 A1 * | 10/2007 | Ahmad et al. .................. 606/73 |
| 2007/0270814 A1 | 11/2007 | Lim et al. |
| 2007/0270860 A1 | 11/2007 | Jackson |
| 2007/0270959 A1 | 11/2007 | Dubousset |
| 2007/0288012 A1 | 12/2007 | Colleran et al. |
| 2008/0021459 A1 * | 1/2008 | Lim ............................ 606/61 |
| 2008/0033433 A1 | 2/2008 | Implicito |
| 2008/0071273 A1 | 3/2008 | Hawkes et al. |
| 2008/0097431 A1 | 4/2008 | Vessa |

FOREIGN PATENT DOCUMENTS

| | | |
|---|---|---|
| GB | 2 420 499 A | 5/2006 |
| WO | WO 98/22050 | 5/1998 |

* cited by examiner

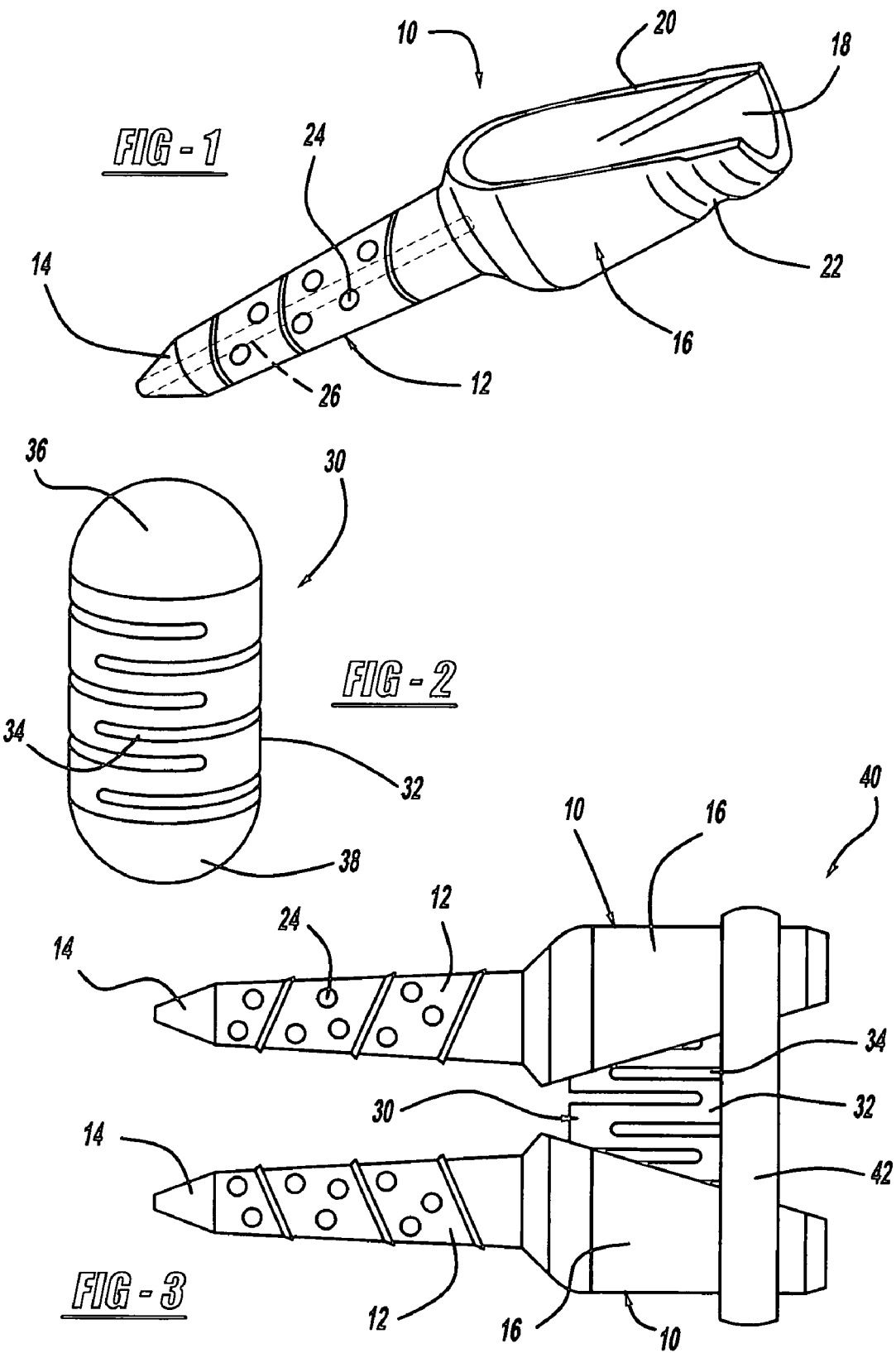

VERTEBRAL DISC ANNULAR FIBROSIS TENSIONING AND LENGTHENING DEVICE

BACKGROUND OF THE INVENTION

1. Field of the Invention

This invention relates generally to a vertebral disc annular fibrosis tensioning and lengthening device and, more particularly, to a vertebral disc annular fibrosis tensioning and lengthening device that employs opposing pedicle screws and a spring member positioned therebetween.

2. Discussion of the Related Art

The human spine includes a series of vertebrae interconnected by connective tissue referred to as intervertebral discs that act as a cushion between the vertebrae. The discs allow for movement of the vertebrae so that the back can bend and rotate.

The intervertebral disc is an active organ in which the normal and pathologic anatomies are well known, but the normal and pathologic physiologies have not been greatly understood. The intervertebral disc permits rhythmic motions required of all vertebrate animals in their various forms of locomotion. The disc is a high-pressure system composed primarily of absorbed water, an outer multilayered circumferential annulus of strong, flexible, but essentially inelastic collagen fibers, and an inner core of a hydrogel called the nucleus pulposus. The swelling of the contained hydrogel creates the high pressure that tightens the annular fibers and its laminations. Degeneration of discs in humans is typically a slow, complex process involving essentially all of the mechanical and physiologic components with loss of water holding capacity of the disc. Discogenic pain arises from either component, but is primarily due to altered chemistry. When this pain is severely disabling and unyielding, the preferred contemporary treatments are primarily surgical, particularly fusion and/or disc replacement.

Annular collagen fibers are arranged in circumferential belts or laminations inserting strongly and tangentially in right- and left-handed angulated patches into each adjacent vertebral body. Inside the annular ring is contained an aggrecan, glycosaminoglycan, a protein-sugar complex gel having great hygroscopic ability to hold water. The swelling pressure of this gel of the nucleus maintains the pressure within the annulus, forcing the vertebrae apart and tightening the annular fibers. This tightening provides the primary mechanical stability and flexibility of each disc of the spinal column. Further, the angulated arrangement of the fibers also controls the segmental stability and flexibility of the motion segment. Therefore, the motion of each segment relates directly to the swelling capacity of the gel and secondarily to the tightness of intact annulus fibers. The same gel is also found in thin layers separating the annular laminar construction, providing some apparent elasticity and separating the laminations, reducing interlaminar torsional abrasion. With aging or degeneration, nucleus gel declines, while collagen content, including fibrosis, relatively increases.

Disc degeneration, which involves matrix, collagen and aggrecan, usually begins with annular tears or alterations in the endplate nutritional pathways by mechanical or pathophysiological means. However, the disc ultimately fails for cellular reasons. As a person ages, the discs in the spine go through a degenerative process that involves the gradual loss of the water holding capacity of the disc, referred to as desiccation. As a result of this loss of water, the disc space height may partially collapse, which may lead to chronic back pain disorders and/or leg pain as a result of the nerves being pinched.

Progressive injury and aging of the disc occurs normally in later life and abnormally after trauma or metabolic changes. In addition to the chemical effects on the free nerve endings as a source of discogenic pain, other degenerative factors may occur. Free nerve endings in the annular fibers may be stimulated by stretching as the disc degenerates, bulges, and circumferential delamination of annular fibers occurs. This condition may lead to a number of problems. It has been shown that a person's disc is typically taller in the morning when a person awakes. This phenomenon may be due in part to the reduction of body weight forces on the disc when lying in a recumbent position overnight that causes the disc height to restore. Therefore, the reduction of compressive forces on the disc may help to restore disc height.

As discussed above, as a person ages, the discs of the spine degenerate, and the disc space height collapses. Further, the ligaments and facets of the spine degenerate as well. These problems lead to a reduction in the foramenal height of the vertebrae, often causing central or lateral canal stenosis. The foramen is an opening through the vertebrae that allows the nerve from the spinal cord to pass through. Because the nerve passes through the foramen, the nerve will often get pinched as the disc height decreases, leading to various types of back pain. Further, these problems often lead to difficulty in walking. Additionally, the lateral canal stenosis causes the nerve to get pinched in the spinal canal. These conditions often lead to neurogenic claudication, where the patient typically responds by walking shorter distances, then sitting down, and then flexing the spine by leaning over or by walking with the aid of a device, which helps to flex the spine.

SUMMARY OF THE INVENTION

In accordance with the teachings of the present invention, a vertebral disc annular fibrosis tensioning and lengthening device is disclosed that restores the loss of disc height as a result of disc degeneration and other factors. In one non-limiting embodiment, the vertebral disc annular fibrosis tensioning and lengthening device includes pedicle screws having screw heads with cup-shaped cavities. The pedicle screws are threaded into the vertebral bodies of adjacent vertebrae through the pedicles so that open parts of the heads of the pedicle screws face each other. A spring is inserted into the cup-shaped cavities in compression so that the spring bias forces the pedicle screws apart, thus increasing the height of the disc space.

Additional features of the present invention will become apparent from the following description and appended claims, taken in conjunction with the accompanying drawings.

BRIEF DESCRIPTION OF THE DRAWINGS

FIG. 1 is a perspective view of a pedicle screw employed in a vertebral disc annular fibrosis tensioning and lengthening device of the invention;

FIG. 2 is a perspective view of a spring employed in the vertebral disc annular fibrosis tensioning and lengthening device of the invention;

FIG. 3 is a side view of the vertebral disc annular fibrosis tensioning and lengthening device of the invention including two of the pedicle screws with the spring therebetween;

DETAILED DESCRIPTION OF THE EMBODIMENTS

Figure 4:
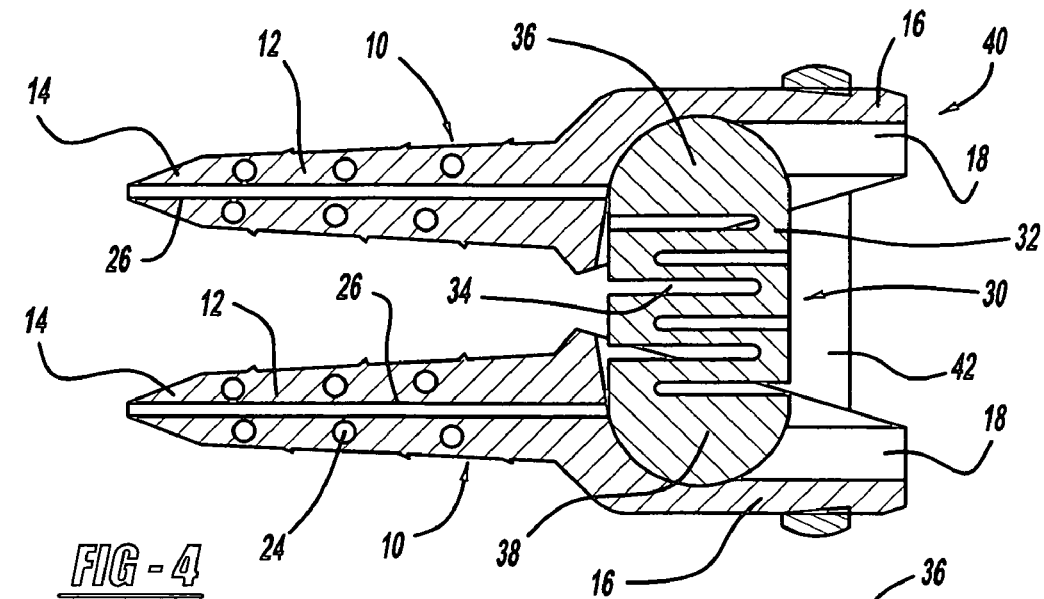
FIG. 4 is a cross-sectional side view of the vertebral disc annular fibrosis tensioning and lengthening device shown in FIG. 3.

The following discussion of the embodiments of the invention directed to a vertebral disc annular fibrosis tensioning and lengthening device is merely exemplary in nature, and is in no way intended to limit the invention or its applications or uses.

FIG. 1 is a perspective view of a pedicle screw 10 for use in a vertebral disc annular fibrosis tensioning and lengthening device (FIG. 3) of the invention. The pedicle screw 10 includes a threaded and tapered body portion 12 having a tip 14. The body portion 12 includes a plurality of holes 24 that allow bone to grow therein when the screw 10 is threaded into the vertebral body so that the pedicle screw 10 is better anchored within the vertebra. The use of holes in the body portion of a pedicle screw to facilitate bone growth therein can be employed in other types of pedicle screws for other uses besides vertebral disc annular fibrosis tensioning and lengthening devices, such as spinal fusion pedicle screw and rod instrumentation, well known to those skilled in the art. The holes 24 can come in a variety of numbers, diameters and configurations. In one non-limiting embodiment, the diameter of the body portion 12 is about 8 mm and the diameter of the holes is about 1.0 mm. The pedicle screw 10 can include a bore 26 that extends through the body portion 12 to make it cannulated so that a K-wire (not shown) can extend therethrough to align the pedicle screw 10, as is well understood to those skilled in the art. The pedicle screw 10 further includes a screw head 16 having an extended cup shape defining a cavity 18. The cavity 18 includes an open side 20 for reasons that will become apparent from the discussion below. An annular recess 22 is formed around an outside of the head 16 also for reasons that will become apparent from the discussion below. The pedicle screw 10 can be made of any suitable material, such as titanium, as would be well understood to those skilled in the art.

FIG. 2 is a perspective view of a spring 30 having a cylindrical body 32 that is also part of the vertebral disc annular fibrosis tensioning and lengthening device of the invention. A series of slots 34 are cut into the body portion 32, as shown, in an alternating configuration that allows the body portion 32 to be compressed and provide an expansive spring force. The spring 30 includes generally rounded ends 36 and 38 that are shaped to conform to the shape of the inner surface of the cavity 18. The spring 30 can be made of any suitable material for the purposes described herein, such as nitinol, which is a flexible metal having a memory. Other materials may also be suitable, such as a shape memory alloy. An example of a suitable alloy includes about 50% nickel and about 50% titanium.

Figure 5:
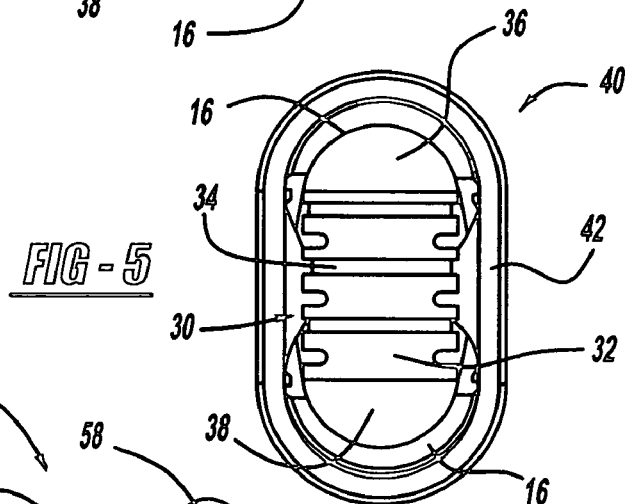
FIG. 5 is a top view of the vertebral disc annular fibrosis tensioning and lengthening device shown in FIG. 3.

FIG. 3 is a side view, FIG. 4 is a cross-sectional view, side view and FIG. 5 is a top view of a vertebral disc annular fibrosis tensioning and lengthening device 40, according to an embodiment of the present invention. The vertebral disc annular fibrosis tensioning and lengthening device 40 includes two of the pedicle screws 10 where the open sides 20 of the heads 16 face each other, as shown. The spring 30 is inserted into the cavities 18 of the heads 16 so that the ends 36 and 38 conform to the inner surface of the cavities 18. The inner surface of the cavities 18 and the ends 36 and 38 can be coated with a suitable low friction material, such as chrome, cobalt, ceramic, etc., to prevent or reduce wear particle formation as the spring 30 and the pedicle screws 10 rub against each other. Initially, the spring 32 is compressed so that it provides an expansive force to separate the pedicle screws 10. In one non-limiting embodiment, the expanded or relaxed length of the spring 30 is in the range of about 3 cm-4 cm, which is about the height of a normal lumbar disc. The diameter of the spring 32 can be any diameter suitable for the purposes described herein.

An oval posterior ring 42 is positioned within the recesses 22, and operates to maintain the screws 10 in their proper orientation, and prevent the pedicle screws 10 from separating beyond a predetermined limit. Further, as the spring 30 causes the pedicle screws 10 to separate, the ring 42 maintains the top end of the pedicle screws 10 stationary to create a pivot and restore the height of the disc. The spring 30 operates as a compressible link and the posterior ring 42 operates as a rigid link.

Figure 6:
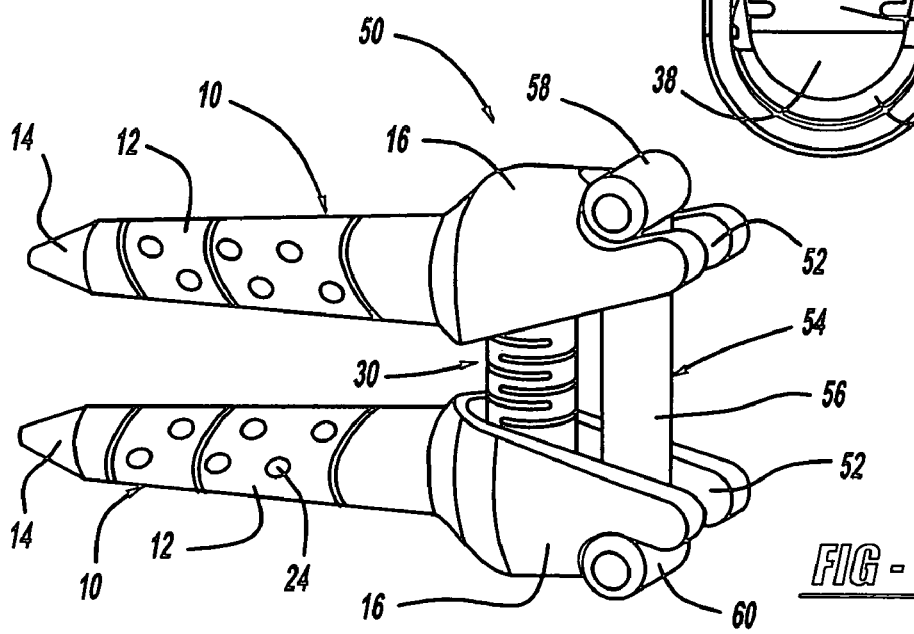
FIG. 6 is a perspective view of a vertebral disc annular fibrosis tensioning and lengthening device, according to another embodiment of the present invention.

FIG. 6 is a perspective view of a vertebral disc annular fibrosis tensioning and lengthening device 50, according to another embodiment of the present invention, where like elements to the vertebral disc annular fibrosis tensioning and lengthening device 40 are identified by the same reference numeral. In this embodiment, the heads 16 of the pedicle screws 10 include a slot 52. The ring 42 is replaced with a dumbbell member 54 including a cylindrical body portion 56 and end portions 58 and 60. The body portion 56 extends through the slots 52 so that the end portions 58 and 60 are positioned on outside sides of the heads 16, and also operates to limit the expansion of the pedicle screws 10 and control the posterior aspects of the screws 10.

Figure 7:
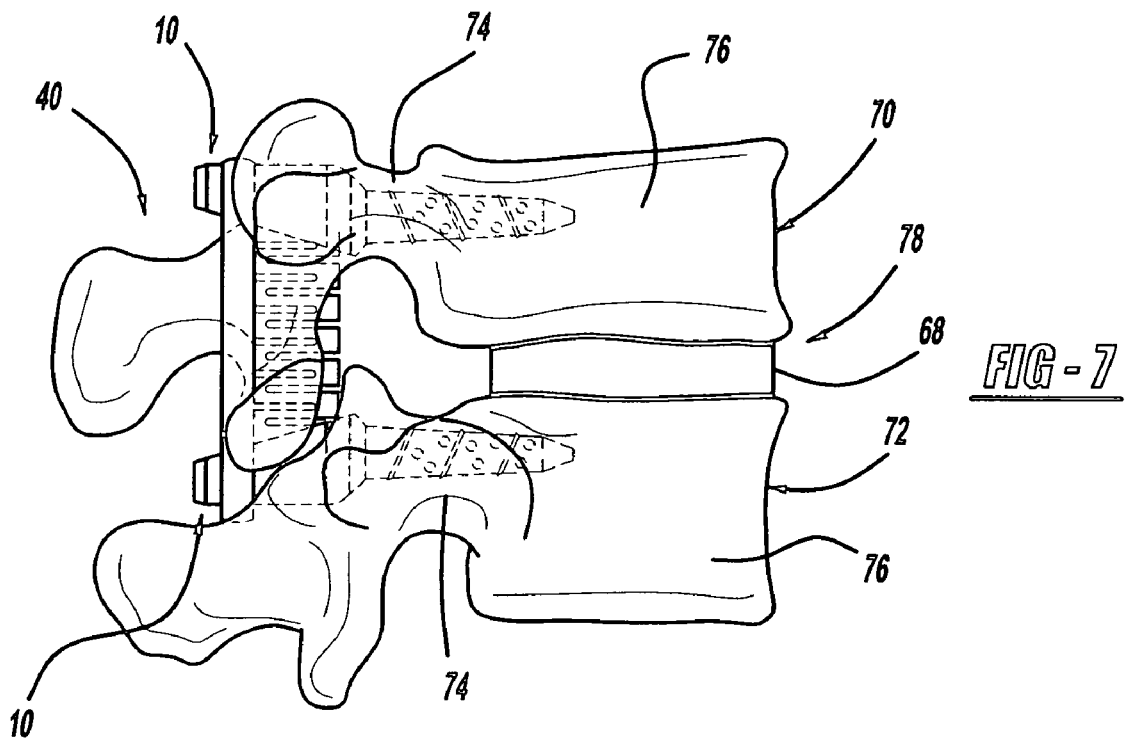
FIG. 7 is a side view showing a vertebral disc annular fibrosis tensioning and lengthening device of the invention inserted within adjacent vertebrae.
Figure 8:
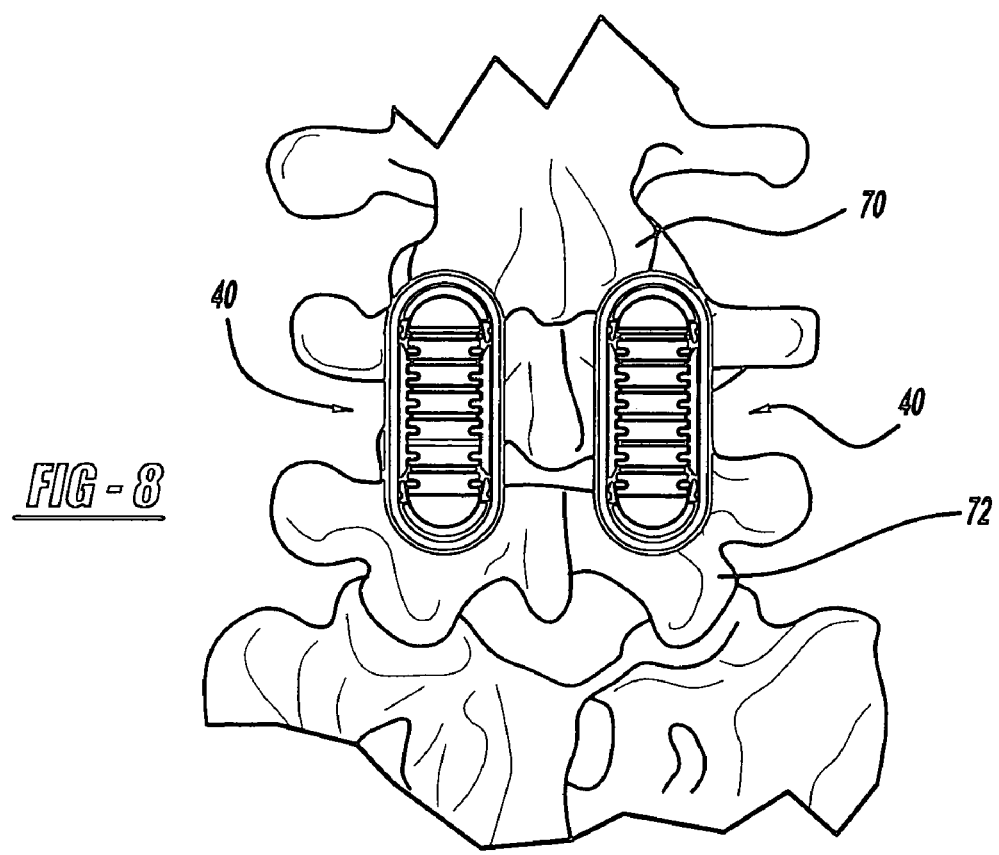
FIG. 8 is a top view of two vertebral disc annular fibrosis tensioning and lengthening devices of the invention inserted within the adjacent vertebrae.

FIG. 7 is a side view and FIG. 8 is a top view of two of the vertebral disc annular fibrosis tensioning and lengthening devices 40 coupled to two adjacent lumbar vertebra 70 and 72 having a disc 68 therebetween. The pedicle screws 10 are threaded through pedicles 74 of the vertebra 70 and 72 and into the vertebral body 76. Once the pedicle screws 10 are in place, then the spring 30 is positioned within the cavities 18 under compression, as discussed above. As the spring bias forces the vertebra 70 and 72 apart, the height of a disc space 78 between the vertebra 70 and 72 increases and is restored. Further, as the height of the disc space 78 increases, the disc 68 is able to regenerate due to reduced sheer or compressive forces applied to the disc 68. The device 40 creates a controlled distraction force and distraction distance on the annulus fibrosis and a controlled dynamic motion of the vertebra. Further, the device 40 allows motion of the spine while maintaining the stress tension effect on the disc 68. Particularly, the device 40 provides a tension force across a compromised vertebral disc providing a distractive force to elicit the stress tension effect on the annulus fibrosis. The pedicle screws and links therebetween are arranged in a parallelogram shape to provide the desired distraction. Because most systems work like a hinge, the front or anterior portion of the disc moves much more than the back or posterior portion of the disc. This is not a natural motion, so with the vertebral linkage of the invention, a parallel or near parallel motion of the disc can be achieved. In one non-limiting embodiment, the motion pathway is an arc of a radius much longer than the pedicle screw length. Although the device 40 is shown coupled to adjacent vertebra, the device 40 can extend across any suitable number of vertebrae to increase the disc space of more than one disc.

Any suitable surgical procedure for placing the pedicle screws 10 can be used, including minimally invasive surgical procedures by making the pedicle screws 10 cannulated. In one known process of percutaneous pedicle screw instrumentation, a Jamshidi needle is used to dock on to the junction of the vertebrae between the facet complex and the transverse process of the vertebra. Gentle taps with a mallet cause the Jamshidi needle to be advanced through the pedicle 74, making sure not to cross the medial border of the pedicle 74, which can result in nerve root injury, until the junction between the pedicle base and the vertebral body is reached. Fluoroscopic visualization into the anterior posterior and lateral planes of the vertebra is used to see the orientation of the Jamshidi needle. The correct trajectory of the Jamshidi needle should place the tip of the needle in the center of the pedicle in the anterior posterior view when the tip of the Jamshidi needle lies at the pedicle vertebral body junction in the lateral view.

Once the junction between the base of the pedicle wall and the vertebral body is reached, the Jamshidi needle can be directed in a more medial fashion. The Jamshidi needle is typically passed to about one-half the depth of the vertebral body, and then a K-wire is passed down the Jamshidi needle and into the vertebral body a little farther to seat it into the bone. The Jamshidi needle is then removed. A series of cannulated muscle dilators are then passed over the K-wire to prevent the soft tissue from going into the threads of the tap. The pedicle is tapped and a cannulated pedicle screw is then passed down the dilators.

Although a specific type of spring has been described above for the vertebral disc annular fibrosis tensioning and lengthening device, the present invention contemplates any suitable linearly expandable link suitable for the purposes described herein. The link exerts a force creating a stress tension effect within the disc allowing it to regenerate according to Wolffs law. The link also allows parallel distraction of the disc, distraction along the coronal plane of the disc tissue, puts the annulus fibrous in tension and provides torsional rotation of the vertebral construct. Further, the pedicle screws can be replaced with any suitable mounting member. By a more general description, the vertebral disc annular fibrosis tensioning and lengthening device includes a caudle vertebral body attachment member and a cephelad vertebral body attachment member having a non-rigid interconnection member therebetween that creates the tension stress effect on the annulus fibrosis. The posterior ring 42 acts as a rigid member coupled between the attachment members, that also operates to provide the distractive force.

Figure 9:
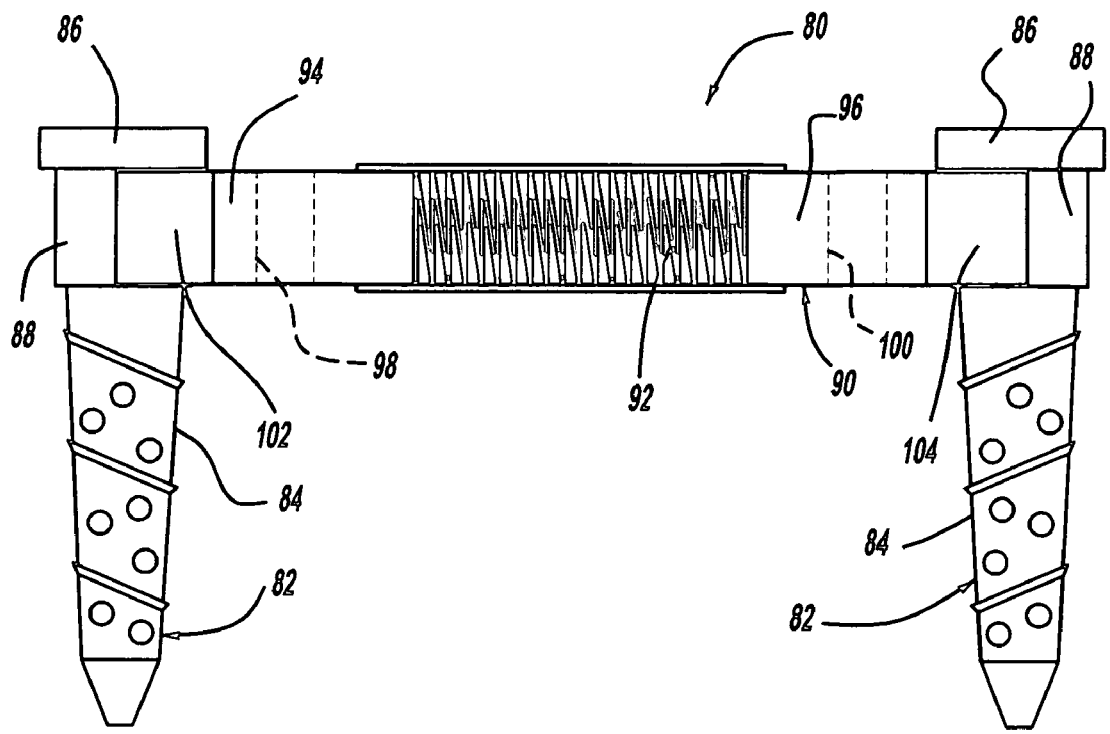
FIG. 9 is a side view of a vertebral disc annular fibrosis tensioning and lengthening device, according to another embodiment of the present invention.
Figure 10:
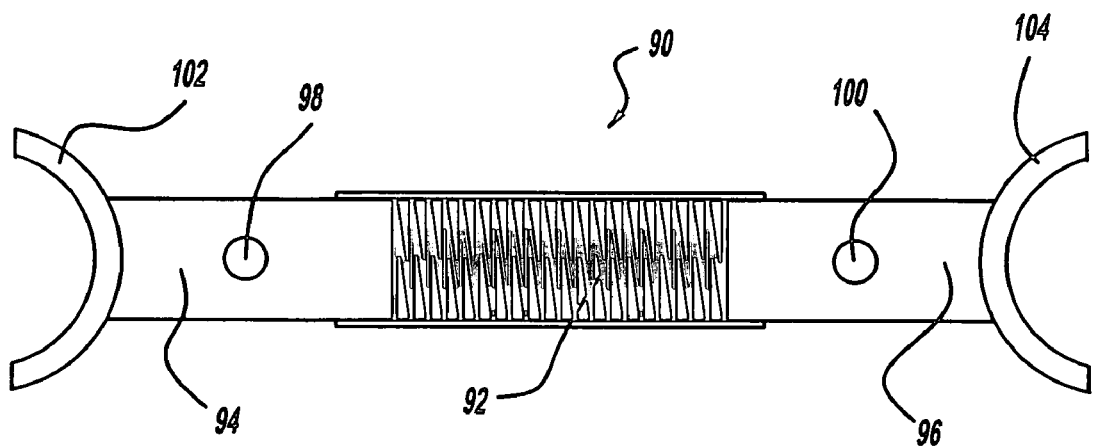
FIG. 10 is a top view of a spring member for the vertebral disc annular fibrosis tensioning and lengthening device shown in FIG. 9.

FIG. 9 is a side view of a vertebral disc annular fibrosis tensioning and lengthening device 80, according to another embodiment of the present invention. The device 80 includes pedicle screws 82 each having a screw body 84 and a screw head 86. An annular mounting portion 88 is provided between the screw head 86 and the screw body 84. The device 80 also includes a spring member 90 having a spring 92 and end plates 94 and 96. FIG. 10 is a top view of the spring member 90. The spring 92 can be any suitable spring, such as a helical spring. Holes 98 and 100 are provided through the end plates 94 and 96, respectively. A U-shaped coupling member 102 is attached to the end plate 94 and a U-shaped coupling member 104 is attached to the end plate 96. The U-shaped coupling members 102 and 104 have a size that conforms to the diameter of the annular mounting portion 88. The surgeon will use a suitable tool (not shown) that is inserted in the holes 98 and 100 to compress the spring 92 and position the U-shaped coupling members 102 and 104 around the annular mounting portions 88 so as to provide a separation force to the pedicle screws 82 for the reasons discussed above.

As discussed above, the pedicle screws 10 include the holes 24 for facilitating bone growth therein. Such a concept eliminates or reduces the halo around the known pedicle screws that reduces the joining of the screw to the bone. With the holes 24, the screw will act more like natural bone and increase the integrity of the bonding between the screw and the vertebra.

The holes 24 are one example for accepting bone growth in a surgical screw. Other configurations can also be employed for pedicle screws, and for other screws permanently placed in a bony structure to provide bone interdigitation. Suitable examples include an non-smooth or porous surface on the screw body, interdigitation cavities formed by the addition of sintered beads on the outside of the screw body, interdigitation cavities formed by laser processing, interdigitation cavities formed by machining grooves, a roughened surface provided by sand blasting, a hydroxyl appetite coating, etc. Further, the screws are not limited to pedicle screws, but can be screws for other surgical applications, such as maxio-facial applications, hip fractures, podiatric fusions and fraction repair, periarticular fracture fixation, arthroplasty device anchoring, long bone fracture repair, cervical fusion construct anchoring, tendon anchoring, etc.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A vertebral disc annular fibrosis tensioning and lengthening device comprising:
    a pair of screws including screw heads, each screw head having a cup-shaped cavity and an open area where the open area of the screw heads face each other;
    a spring positioned between the screws along a first axis, said spring including opposing ends that are positioned within the cup-shaped cavity of the screw heads, said spring applying a bias to the screws that causes the screws to separate; and
    a rigid posterior ring positioned around an outside of the heads along a second axis, said first and second axes being offset from each other so that the spring causes the screws to pivot away from each other at the second axis.

2. The device according to claim 1 wherein the spring includes a cylindrical body between the opposing ends.

3. The device according to claim 2 wherein the cylindrical body includes a plurality of spaced apart slots that allow the spring to be compressed.

4. The device according to claim 1 wherein the ring is positioned within an annular recess in the heads.

5. A vertebral disc annular fibrosis tensioning and lengthening device for increasing the height of an intervertebral disc, said device comprising a pair of support members mounted to vertebrae, a linearly expandable link member positioned between and in contact with the support members along a first axis and a rigid member positioned between and in contact with the su ort members on a second axis said first and second axes being offset from each other, said link member applying a bias to the support members that causes the support members to separate and pivot at the second axis so as to provide a distractive force to the disc.

6. The device according to claim 1 wherein an inner surface of the cavity in the screw heads includes a low friction material to reduce wear particle formation.

7. The device according to claim 1 wherein the screws are pedicle screws effective to be threaded through a pedicle of a vertebra and into a vertebral body.

8. The device according to claim 1 wherein the screws include a screw body, said screw body including recesses for accepting bone growth.

9. The device according to claim 1 wherein the spring has a length in the range of 3 cm-4 cm.

10. The device according to claim 1 wherein the screws are cannulated.

11. The device according to claim 1 wherein the spring is made of a memory alloy.

12. The device according to claim 11 wherein the spring is made of nitinol.

13. A vertebral disc annular fibrosis tensioning and lengthening device for increasing the disc space between adjacent vertebra, said device comprising:
  a pair of pedicle screws including screw heads, each screw head having a cup-shaped cavity and an open area where the open area of the screw heads face each other, each screw head further comprising an outer recess;
  a spring member positioned between the screws along a first axis, said spring member including a cylindrical body having generally rounded ends that are positioned within the cup-shaped cavity of the screw heads, said cylindrical body including a plurality of spaced apart slots that allow the spring member to be compressed, said spring member applying a bias to the screws that causes the screws to separate; and
  an oval shaped rigid posterior link positioned within the recesses in the heads along a second axis, said first and second axes being offset from each other so that the spring causes the screws to pivot away from each other at the second axis.

14. The device according to claim 13 wherein an inner surface of the cavity in the screw heads includes a low friction material to reduce wear particle formation.

15. The device according to claim 13 wherein the screws include a screw body, said screw body including recesses for accepting bone growth.

16. The device according to claim 5, wherein the rigid member is a dumbbell member, said support members including a slot where an end of the dumbbell member is positioned within the slots.

17. The device according to claim 16 wherein the link member is a cylindrical member coupled to heads of the support members, said link member including a cylindrical body having slots that allow the link member to be compressed.

18. The device according to claim 16 wherein the link member includes an elongated portion having a spring and end plates, said end plates including openings, said link member further including U-shaped members at the end of each end plate, said U-shaped members being positioned in contact with the support members.

19. A vertebral device comprising a caudal vertebral body attachment member, a cephelad vertebral body attachment member, a non-rigid interconnection member coupled to the caudal vertebral body attachment member and the cephelad vertebral body attachment member, a rigid interconnection member coupled to the caudal vertebral body attachment member and the cephelad vertebral body attachment member at a location separate from where the non-rigid interconnection member is coupled to the caudal vertebral body attachment member and the cephelad vertebral body attachment member so that the non-rigid interconnection member causes the caudal vertebral body attachment member and the cephelad vertebral body attachment member to separate and pivot relative to each other at the location where the rigid interconnection member is coupled to the caudal vertebral body attachment member and the cephelad vertebral body attachment member, wherein the interconnection member creates a tension stress on an annulus fibrosis between vertebra.

20. The device according to claim 19 wherein the device provides a controlled distraction force and a controlled distraction distance on the annulus fibrosis and a controlled dynamic motion of the vertebra.

21. The device according to claim 19 wherein the interconnection member allows vertebral motion while maintaining stress tension on the annulus fibrosis.

22. A vertebral device comprising a caudal pedicle screw, a cephelad pedicle screw, a rigid link coupled to the caudal pedicle screw and the cephelad pedicle screw and a compressible link coupled to the caudal pedicle screw and the cephelad pedicle screw, wherein the rigid link and the compressible link are coupled to the caudal pedicle screw and the cephelad pedicle screw so that the compressible link causes the caudal pedicle screw and the cephelad pedicle screw to separate and pivot at the location where the rigid link is coupled to the caudal pedicle screw and the cephelad pedicle screw, wherein the rigid link and the compressible link provide a distractive force to an annulus fibrosis between vertebra.

23. The device according to claim 22 wherein the device provides a controlled distraction force and a controlled distraction distance on the annulus fibrosis and a controlled dynamic motion of the vertebra.

24. The device according to claim 22 wherein the links and the pedicle screws are arranged in a parallelogram shape.

25. The device according to claim 22 wherein the links allow vertebral motion while maintaining stress tension on the annulus fibrosis.

26. The device according to claim 25 wherein the motion pathway is an arc having a radius much longer than a length of the pedicle screws.

* * * * *